United States Patent
Lamont et al.

(10) Patent No.: US 6,897,026 B2
(45) Date of Patent: May 24, 2005

(54) ARRAY IMAGING METHOD

(75) Inventors: John Victor Lamont, Co. Antrim (IE); Robert Ivan McConnell, Co. Antrim (IE); Stephen Peter Fitzgerald, Co. Antrim (IE)

(73) Assignee: Randox Laboratories Ltd., Co Antrim (IE)

( * ) Notice: Subject to any disclaimer, the term of this patent is extended or adjusted under 35 U.S.C. 154(b) by 0 days.

(21) Appl. No.: 10/046,728

(22) Filed: Jan. 17, 2002

(65) Prior Publication Data
US 2002/0146847 A1 Oct. 10, 2002

(30) Foreign Application Priority Data
Jan. 30, 2001 (GB) .............................................. 0102357

(51) Int. Cl.[7] .......................... C12Q 1/68; G01N 21/47; C12M 1/36; C07H 21/04
(52) U.S. Cl. ......................... 435/6; 435/174; 435/283.1; 435/287.2; 422/68.1; 422/82.05; 422/82.08; 536/23.1; 536/24.3; 530/300; 530/358
(58) Field of Search ............................. 422/68.1, 82.05, 422/82.08, 63; 435/174, 6, 283.1, 287.2; 536/23.1, 24.3; 530/300, 350, 387.1; 436/43, 46

(56) References Cited

U.S. PATENT DOCUMENTS 5,143,854 A * 9/1992 Pirrung et al. ............... 436/518
5,356,785 A    10/1994 McMahon et al.
5,432,099 A     7/1995 Ekins
5,578,832 A *  11/1996 Trulson et al.
5,721,435 A     2/1998 Troll
5,974,164 A    10/1999 Chee
6,090,555 A *   7/2000 Fiekowsky et al. ............ 435/6
6,309,601 B1 * 10/2001 Juncosa et al.
6,362,004 B1 *  3/2002 Noblett

FOREIGN PATENT DOCUMENTS

| | | |
|---|---|---|
| GB | 2 324 866 A | 11/1998 |
| GB | 2 351 556 | 1/2001 |
| WO | WO 91/19274 | 12/1991 |
| WO | WO 95/16204 | 6/1995 |
| WO | WO 98/49543 | 11/1998 |

* cited by examiner

*Primary Examiner*—B J Forman
(74) *Attorney, Agent, or Firm*—Oliff & Berridge, PLC

(57) ABSTRACT

A method for imaging molecules contained in an array of discrete reaction sites on the surface of a solid support comprises:

(i) imaging the array and detecting a first molecule located on the solid support at a known position with respect to the array;

(ii) by reference to the first molecule, aligning inspection windows in registration with the discrete reaction sites; and (iii) determining the amount of detectable signal in each window.

The method is used to locate the reaction sites accurately on the array, and to correct for any misalignments.

12 Claims, 8 Drawing Sheets

ARRAY IMAGING METHOD

FIELD OF THE INVENTION

This invention relates to a device and apparatus for performing multi-analyte assays.

BACKGROUND OF THE INVENTION

There is now widespread interest in the use of fabricated arrays of molecules in the detection and characterisation of analytes. For example, fabricated arrays of polynucleotides are now used widely in DNA sequencing procedures and in hybridisation studies for the detection of genetic variations in a patient.

The fabricated arrays can be designed to include high densities of the same or different molecules immobilised on a solid support surface. This allows the user to generate many results in one experimental procedure. The arrays also have the advantage in that the analytical methods can be automated, thereby allowing a high throughput of samples to be achieved.

The arrays are usually designed with a plurality of individual reactions sites located in spatially-distinct areas on a solid support. In order to produce the arrays in spatially-distinct areas, the most common approach has been through photolithographic techniques. The solid support is coated with a photolabile linker, which only becomes reactive towards a binding ligand following irradiation with light of a suitable wavelength. Spatial resolution is achieved by placing a physical mask on the solid support surface. The pattern of holes in the mask determines the pattern of binding regions on the solid support.

WO-A-95/16204 describes a photolithographic approach using avidin and the photolabile molecule photobiotin. Spatial resolution has also been achieved by passive adsorption. For example, U.S. Pat. No. 5,432,099 discloses binding of the molecules to the solid support surface through a combination of ionic interactions, hydrophobic interactions and Van Der Waals forces.

One particular example of fabricated arrays concerns solid support materials immobilised with nucleic acids. These arrays consist typically of a high-density matrix of polynucleotides immobilised in spatially-distinct regions. Fodor et al Trends in Biotechnology (1994) 12:19–26, describes ways of assembling the nucleic acids using a chemically sensitised glass surface protected by a mask, but exposed at defined areas to allow attachment of suitably modified nucleotide phosphoramidites. Stimpson et al, PNAS (1995) 92:6379–6383, describes the manufacture of fabricated arrays by the technique of "spotting" known polynucleotides onto a solid support at predetermined positions.

In order to maximise the potential and the sample throughput using the array technology, it is essential to fully automate the signal processing from the reaction sites of the arrays. Therefore, it is necessary to perform the imaging of the array, and further mathematical processing of that image, without manual intervention. A difficulty that is experienced with fully automated systems is that each reaction site is sometimes difficult to locate accurately. This may be due to the nature of the array manufacturing process, where it is not possible for the array to be in exactly the same position on each device. The problems may also be due to slight movement of the devices in the apparatus, which may be caused during the washing steps necessary in the assay procedure. As each distinct reaction site may be separated by a distance of only 10–50 µm, it is difficult to ensure that the automated system has accurately positioned each reaction site. For example, movement of the array can be of the same order of magnitude as the distance between each reaction site. This means that predefined windows in the image, for each reaction site to be analysed, cannot be easily used, as the movements may cause the wrong reaction site to fall inside an inspection window which defines the boundary of the reaction site. Alternatively, a reaction site may be missed by the windows, or possibly two sites may fall within the same window. To make processing easier, it is necessary to ensure that only one reaction site falls wholly within each analyte inspection window.

There is therefore a need for improved methods which allow accurate positioning of each discrete reaction site on an array.

SUMMARY OF THE INVENTION

The present invention is based on the realisation that accurate positioning of individual reaction sites on an array can be carried out by incorporating a reference molecule on each array.

According to a first aspect of the invention, a method for imaging molecules contained in an array of discrete reaction sites on the surface of a solid support, comprises, (i) imaging the array and detecting a first molecule located on the solid support at a known position with respect to the array;

(ii) by reference to the first molecule, aligning inspection windows in registration with the discrete reaction sites; and (iii) determining the amount of detectable signal in each window.

The method allows accurate positioning of the inspection windows, thereby providing improvements to conventional automated systems.

As the first molecule is in a known position on the solid support with respect to the array, it is possible to align the inspection windows to be in registration with the arrayed reaction sites.

DESCRIPTION OF THE INVENTION

Figure 1:
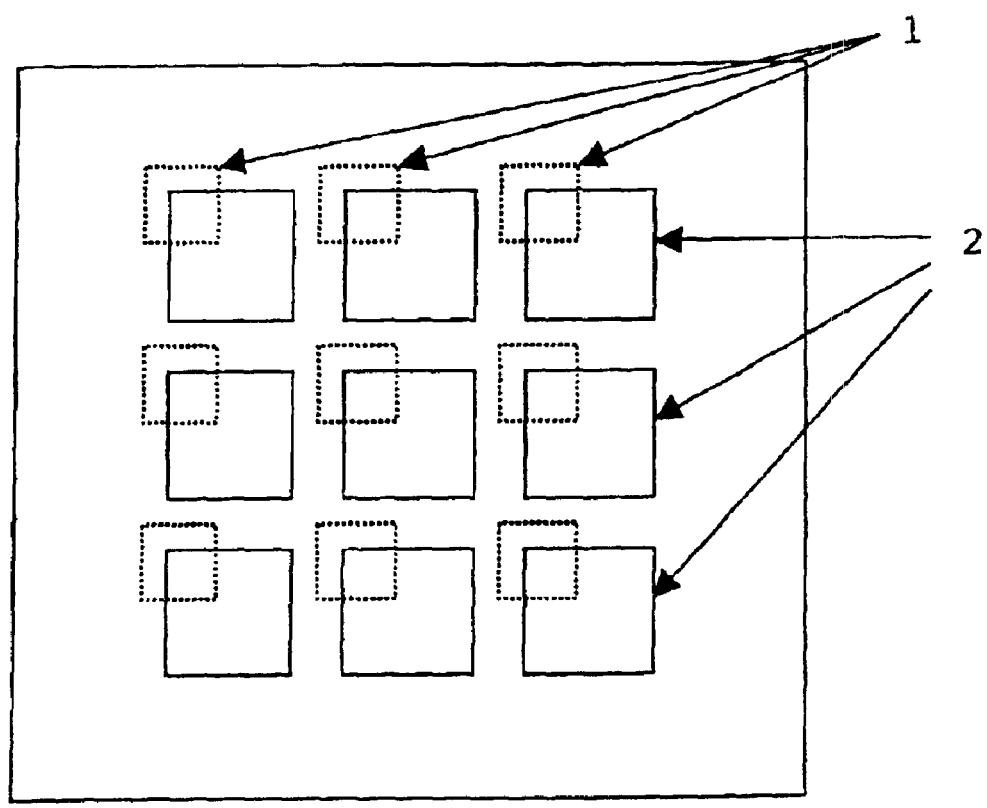
FIG. 1 is a schematic illustration of an array of biochips, with each biochip (2) imaged within a reference molecule search window (1)

The present invention makes use of conventional apparatus to accurately image arrayed molecules. Using a conventional imaging apparatus, the solid support or "biochip" is imaged using, for example, an optical microscope or a charge-coupled device. The image is digitised by camera electronics into (for example) 512×512 pixels, of 16 bits per pixel, and transferred to a computer with an analyser, for processing. In order to accurately position each reaction site on the biochip, the reference molecule (or first molecule) is first located and an array of analyte inspection windows established with respect to the reference molecule (FIG. 1). The positioned inspection windows are then used to find the reaction sites or "analyte spots" on the biochip.

The term "inspection window" is used herein to refer to a defined boundary that encompasses a two-dimensional array of pixels, used to image a detectable signal.

The reference molecule may also be used as an on-chip quality control check, so that, if the intensity of the detectable signal is outside of a pre-defined range, e.g. because of biochip preparation, the biochip results may be rejected.

Figure 2:
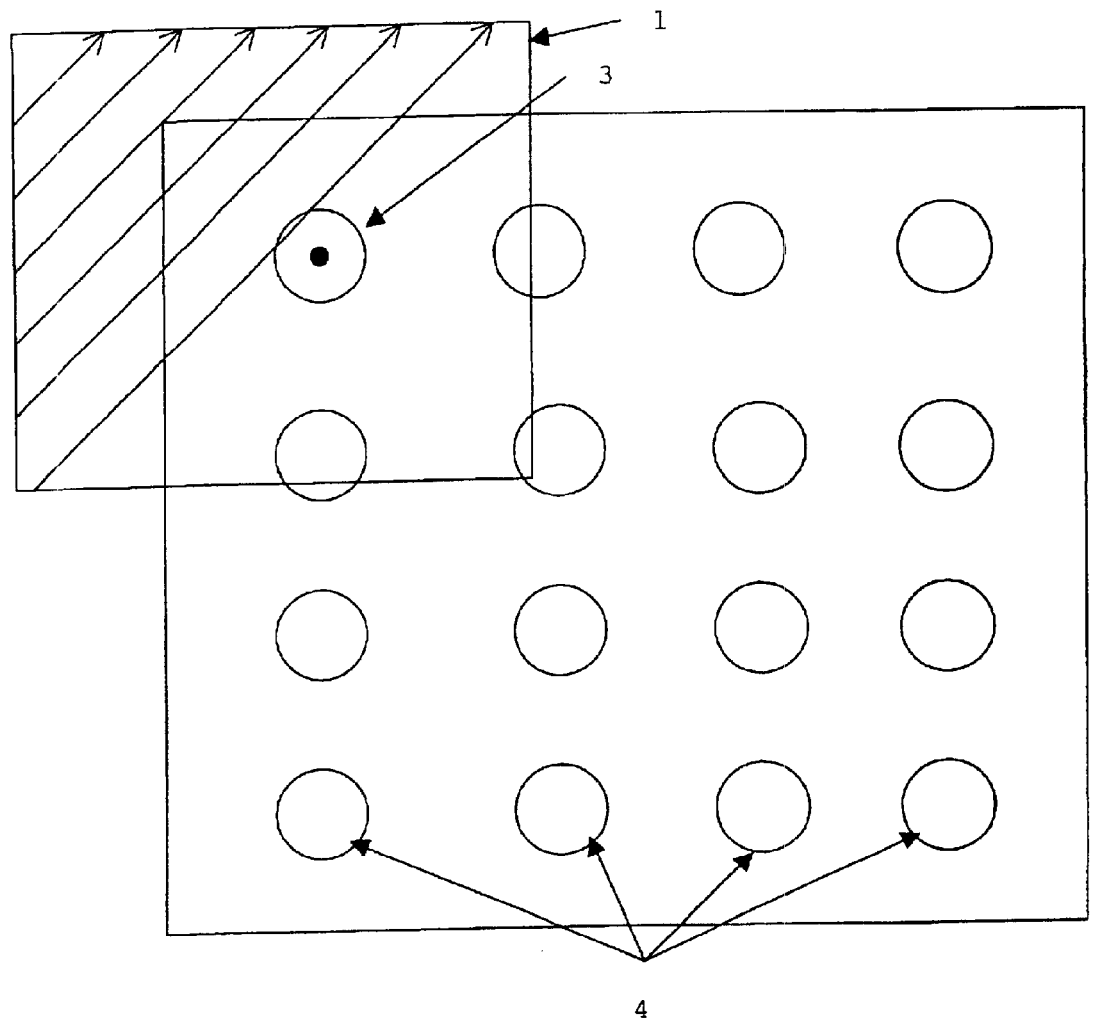
FIG. 2 shows an individual biochip (2) having a reference molecule (3) and an array of analyte reaction sites (4)

The reference molecule should be located at a pre-defined position on each biochip. For example, a reference molecule may be located in one or more corners of the biochip. Therefore, one or more inspection windows may be defined in fixed locations, corresponding to the expected reference molecule locations. The manufacturing tolerances are such that the reference molecule can fall within a somewhat larger search inspection window than the reaction site or analyte inspection window, even though one or more reaction sites from the array may also fall inside the reference molecule inspection window. The search strategy, used to find only each reference molecule in the inspection window, and ignoring other reaction sites must be chosen to ensure that the reference molecule is found first. For example, if a reference molecule is located in the top left corner of each biochip, then a diagonal search, starting in the top left corner of the inspection window, will encounter the reference molecule first, and so allow it to be correctly identified (FIG. 2). For other reference locations, the search strategy can be adjusted accordingly. Searching may be carried out using conventional software to move the search inspection window across the solid support to locate and be in registration with the reference molecule.

Figure 3:
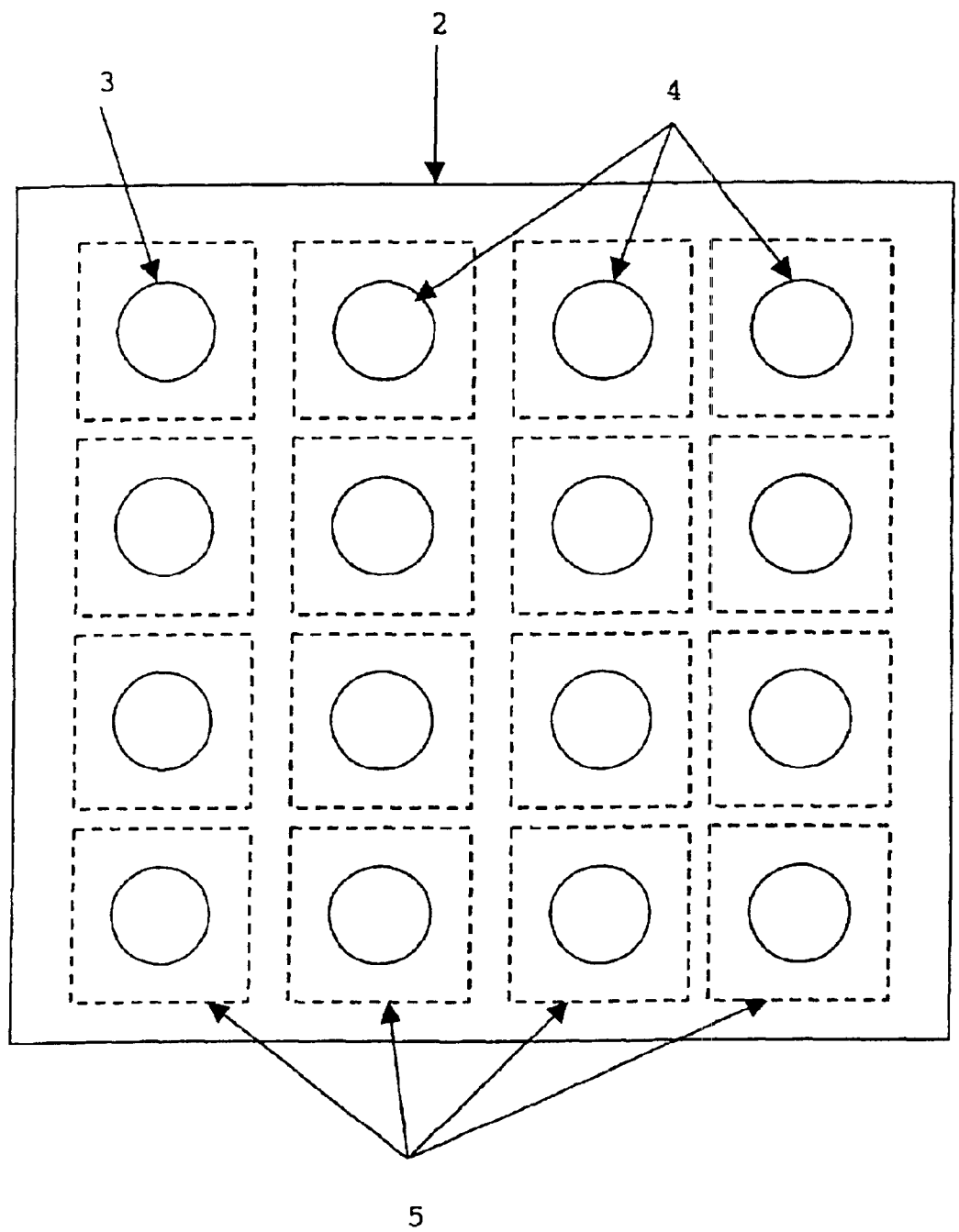
FIG. 3 shows the alignment of the analyte inspection windows (5) in registration with the analyte reaction sites (4)

Once the reference molecule position is identified, the analyte inspection windows may be positioned with respect to it (shown as (5) in FIG. 3). This is aided either by the use of a second reference molecule located at a known position or by the knowledge that the first reference molecule is positioned in a fixed position with respect to the array of reaction sites. Locating the reference molecule allows the position of each reaction site of the array to be determined.

Figure 4:
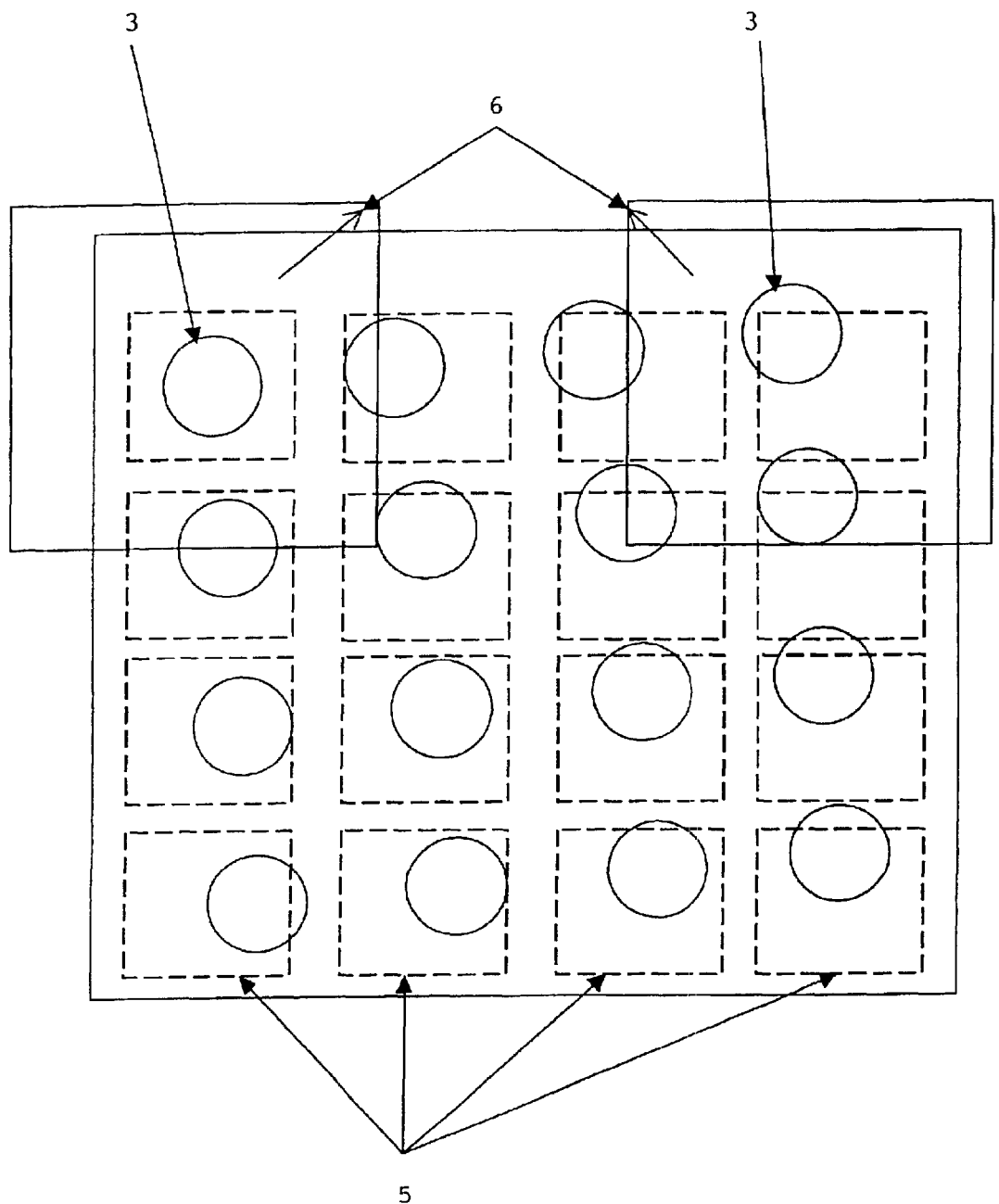
FIGS. 4 and 5 show a biochip that has two reference molecules (3) which can be used to position the inspection windows (5) into correct registration with the reaction sites.
Figure 5:
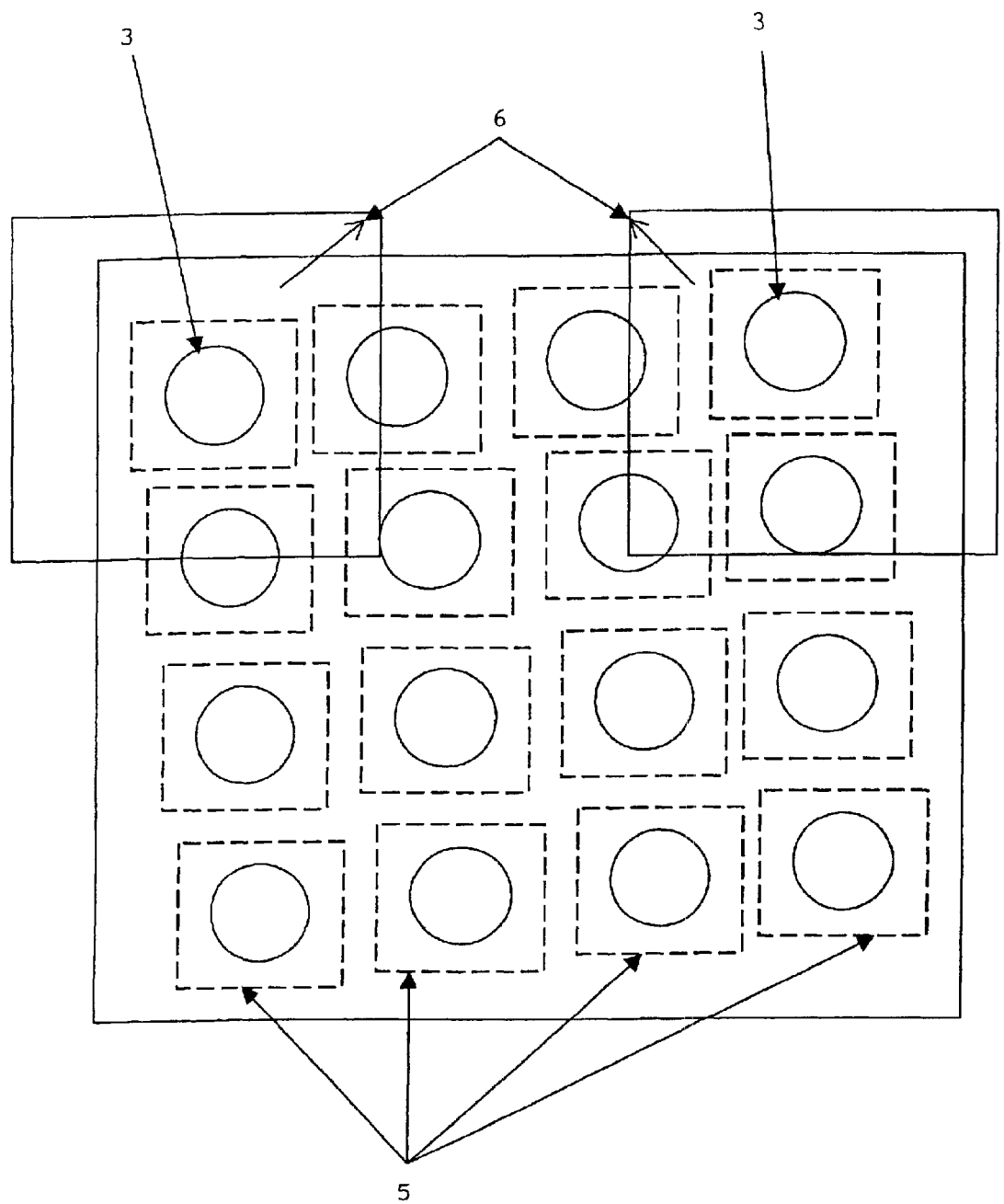

In a preferred embodiment, the biochip comprises two reference molecules. Having two reference molecules has the further advantage that, once the coordinates of each are determined, adjustments can be made for the alignment of the inspection windows. This is most clearly illustrated in FIGS. 4 and 5. The degree to which the second reference molecule varies with respect to the first reference molecule and its expected position can be calculated and used to determine the extent of rotation or misalignment of the biochip. This enables more accurate positioning of the analyte inspection windows. In FIG. 4, (6) represents the direction for the search carried out within the reference molecule inspection window.

The coordinates of the reference molecule(s) on the biochip are used to position the inspection windows for the discrete reaction sites containing the molecules to be analysed. Processing of the signal determines the amount of detectable signal, and thereby the level of reaction at that site. Processing may be carried out using conventional techniques, including confocal microscopy or charge-coupled devices (CCD). In a preferred embodiment, the biochip device is used in a system having a charge-coupled device to visualise the array.

The image may be processed as follows. The imaging device is used to generate an image which is copied to a processor. Several conventional morphological smoothing operations may then be performed on it, to generate a smoothly varying background image. This is then subtracted from the original image to give the background-corrected image. A conventional thresholding operation may be performed on the image data, to create a binary image, by segmenting the image into white, for those areas above the threshold, and black for those below the threshold, where the threshold is chosen at an appropriate level to find the reference molecule.

The segmented reference molecule(s) should form discrete contiguous 'blobs'. 'Blob' analysis, a term used conventionally to describe the processing of such discrete segmented regions, is used to find those pixels which form part of the reference molecule(s), within a pre-defined inspection window. 'Blob' analysis, typically, uses a contour-following operator to follow the outline of a segmented region, so that a closed boundary is formed. Common in digital image processing, or contour following, is the chain code or Freeman code, which dates from 1961. This code, and variants thereof, may be used to calculate the perimeter and size of a segmented object, and such parameters may be used to verify that the size and shape of the segmented blobs fall within the expected limits for the reference molecule. If the 'blob' is too small, too large, or the wrong shape (e.g. ratio of length to height, or circularity), it may be rejected—this allows for cosmic ray artefacts, stray reflections from the biochip walls, sections of other analyte spots intruding into the window, etc., to be ignored.

Commercial programs using 'blob' analysis include IMAQ Vision Software from National Instruments, and CVC from Stemmer Imaging; other programs, such as Neurocheck4.2, from Data Translation Ltd., use a different terminology (referring to regions of interest rather than blobs), but perform essentially the same operations on the pixel data for measurements of areas found by various search strategies.

For a reference molecule located in or near the corner of a biochip analyte array, a diagonal search of the binarised reference inspection window (in a direction appropriate to ensuring that the reference molecule is found first), would be used to locate the first pixel that falls above the threshold, along the diagonal line, and the connectedness to other above-threshold pixels may be determined in the vicinity of this pixel. If it is connected directly to a sufficient number of other above-threshold pixels, it may be considered to form part of the boundary of the reference molecule. The search continues to locate all above-threshold pixels forming part of the boundary, and the chain code is used to close the boundary, starting and finishing at the first boundary pixel, and, thus, identifying only the pixels that form the reference molecule.

The pixels that are found to fall on or within the closed boundary, can then have their central positions calculated for each reference window, and these central positions can then be used to define the locations of the analyte inspection windows. When the analyte inspection window positions are determined, the image data within these may be analysed similarly to determine those pixels that form each of the discrete test reaction sites (DTRs), which determine the discrete regions of arrayed molecules (reaction sites). The background-corrected image intensities for each of these reaction site segmented 'blobs' may then be processed further to calculate the signal at each of these locations and, therefore, the degree of biochemical reaction that has occurred at each reaction site.

Typically, to calculate the signal for those pixels identified for each reaction site, the maximum intensity for each site is found, and then all pixels having an intensity within an empirically determined range, e.g. 20% below each maximum, will be used to measure the signals. Such a signal measurement may be a simple summation of all pixel intensities, within the previous limits, or, possibly, an average thereof, for each reaction site. An example of a preferred imaging process is disclosed in EP-A-0902394, the content of which is incorporated herein by reference.

Figure 6:
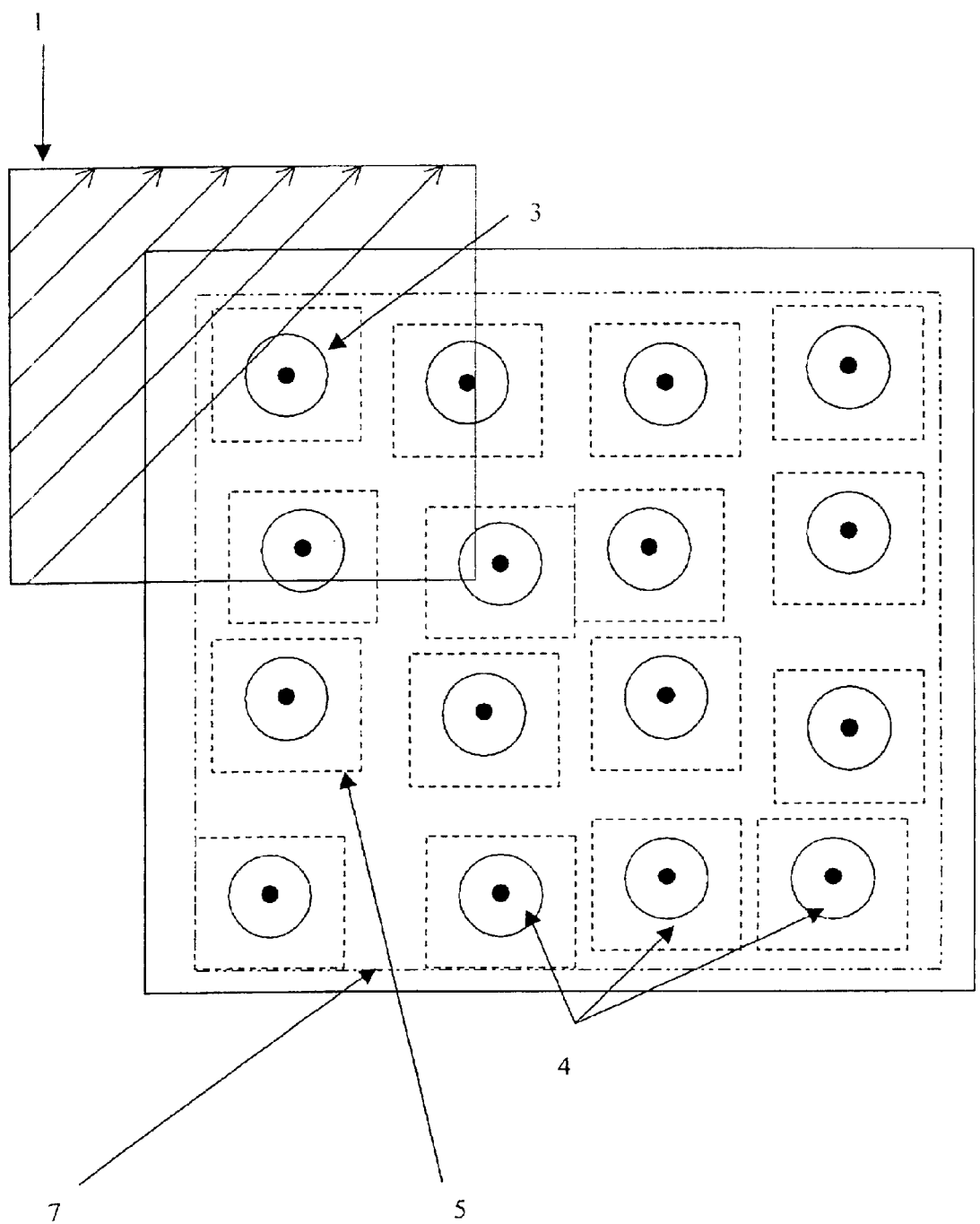
FIG. 6 shows a diagonal search for the reference molecule within the reference molecule search window.

The array of discrete reaction sites may not always be aligned in a regular pattern. To correct for any misalignments, it may be preferable, once the reference molecule has been located, to align an analyte inspection window so that all the possible reaction sites are located within the one window (see (7) of FIG. 6). Imaging using blob analysis will reveal the closed contours of the reaction sites and will permit an individual inspection window to be aligned for each reaction site, so that the central positions can then be calculated.

Figure 7:
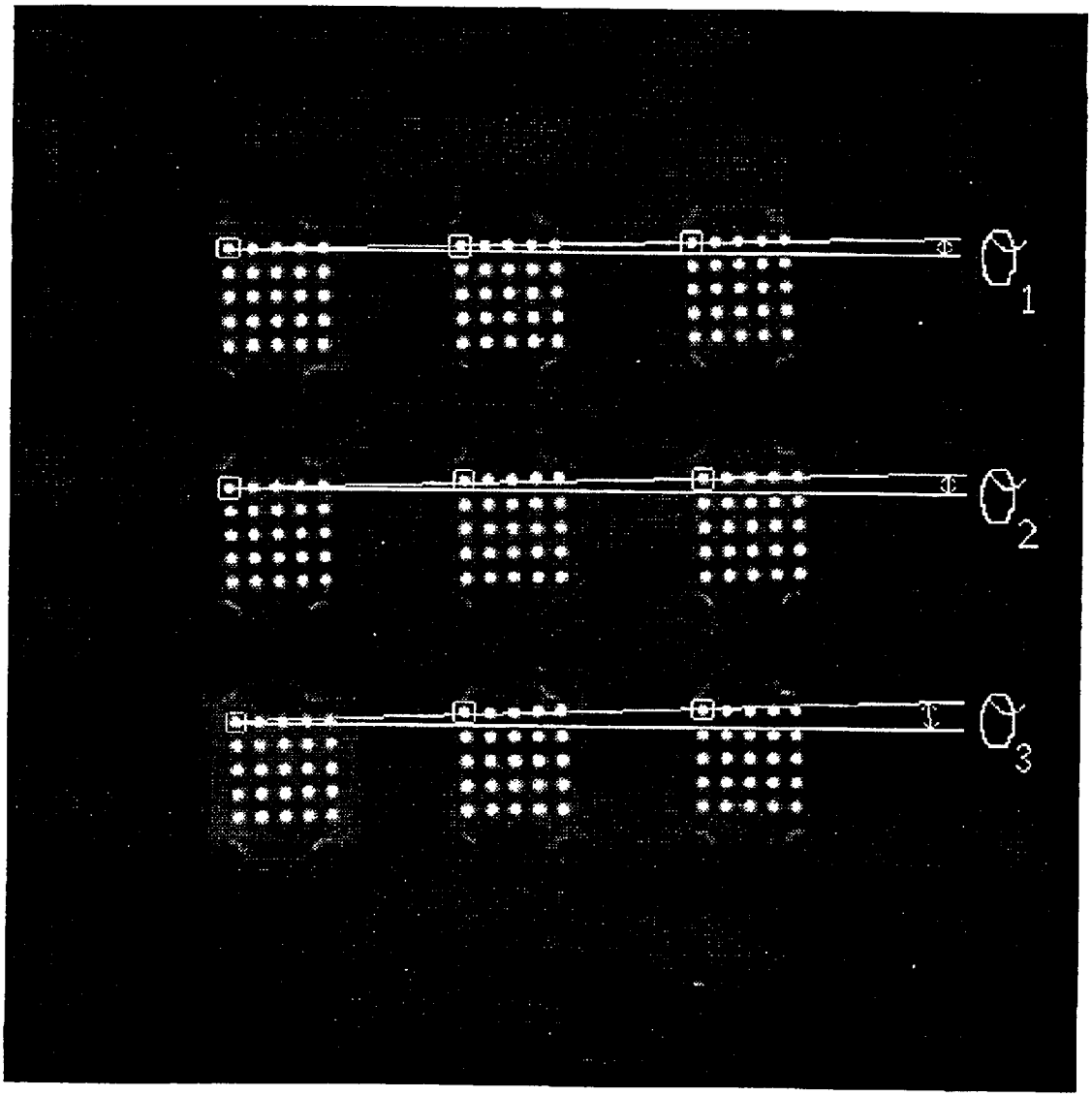
FIG. 7 shows several biochips aligned in one rack, with the degree of rotation of the rack calculated using a single reference molecule on each biochip.

In an alternative embodiment, the relative coordinates of the reference molecule in different biochips may be used to calculate the degree of rotation or misalignment. This is most simply illustrated in FIG. 7, where multiple biochips are located within a single rack. Calculating the position of each reference molecule relative to each other and the expected alignment from one of the reference molecules allows the degree of rotation to be calculated. The inspection windows can then be aligned in correct registration with each reaction site.

The solid support material which is used in a device of this invention may be, for example, silicon, plastic, membrane forming materials, quartz, glass or ceramic materials (aluminium oxide). Ceramic materials provide an excellent alternative to silicon, since both fluorescent and chemiluminescent detection techniques can be employed successfully.

The solid support material used in the invention may be less than 1 cm$^2$. The discrete regions of immobilised molecules may be separated by less than 200 μm, preferably less than 100 μm, and most preferably 10–15 μm.

Preferred devices which may be used in the invention are described in GB-A-2324866, the content of which is incorporated herein by reference.

The molecules used in the invention, may be immobilised on the surface of the material using conventional means. Covalent immobilisation is preferred. Passive adsorption may also be used, but this form of immobilisation is susceptible to changes in pH, temperature and ionic strength, and may in some instances result in release of weakly-bound molecules during incubation and washing steps, thus contributing to poor reproducibility. It is of course desirable that the molecules retain maximum activity, after the immobilisation procedure.

Covalent immobilisation of the molecules may be carried out using conventional techniques, typically using a chemically-reactive linker molecule, which can be activated under defined conditions. Examples of suitable linker molecules are described in GB-A-2324866.

The molecules immobilised to the solid support material may be any suitable for use in an analyte assay. For example, the arrayed molecules may be polynucleotides, e.g. DNA, RNA, or functional analogues thereof. Alternatively, proteins and peptides may be used, e.g. enzymes, antibodies, receptors or hormones. The molecules may also be viruses or an organic compound.

The reference molecule may be visualised by various techniques, including calorimetric, chemiluminescent, fluorescent or bioluminescent means. The molecule may therefore be any entity which is capable of generating or facilitating the generation of a detectable signal. In one embodiment, the molecule is a fluorescent label which is bound to the device.

Suitable fluorescent labels will be known to the skilled person. Examples include: rhodamine, CY-5, fluorescein, fluorescein isothiocyanate and oregon green.

The fluorescent label may be attached directly to the solid support using chemical means. Alternatively, the fluorescent label may be attached indirectly via an immobilised linker molecule, e.g. a protein, or antibody molecule, or through hybridisation with complementary polynucleotides. Alternatively, a labelled polynucleotide may be used without the requirement for hybridisation.

Alternatively, the molecule may be a biological molecule capable of interacting with a ligand to generate a detectable signal. An example of a suitable biological molecule is an enzyme, e.g. horseradish peroxidase, luciferase or β-galactosidase. Each of these enzymes is capable of participating in a biological reaction which generates a detectable signal. In an alternative embodiment, an antibody is used as the reference molecule and in use, the antibody binds to a ligand which is itself detectable. For example, the antibody may have affinity for the enzyme horseradish peroxidase, which is able to undergo a chemiluminescent process to generate the detectable signal. Preferably, the reference molecule does not react with the analytes which are brought into contact with the arrayed molecules on the solid support. Furthermore, the reference molecule should always be detectable, irrespective of the other analyte reactions that are carried out on the solid support. It is preferable therefore that the reference molecule is chosen to be independent from those molecules undergoing reaction in the analyte assay.

The method of the invention is preferably carried out by automated means, controlled by a suitably programmed computer.

The following Example illustrates the invention.

EXAMPLE

In this experiment, a series of 9 mm$^2$ multi-analyte biochips (retained in a 3×3 grid in a rack) were prepared by deposition of 19 antibody spots on 19 discrete locations per biochip in a 5×5 grid, using proprietary deposition equipment. The biochips were incubated at 37° C. after deposition to ensure covalent bonding of the antibodies to the biochip surface. The biochips were then immersed in a blocking solution, which attached to the non-spotted areas of the biochip, thus preventing non-specific binding to the areas outside of the antibody spots (DTRs).

The grid of analyte spots used on each biochip was as shown below, with abbreviations explained in the following text:

| FITC/REF | Barb   | Benzo   | Loraz | THC     |
|----------|--------|---------|-------|---------|
| Amph     | MA     | Methad  | PCP   | FITC(1) |
| FITC(2)  | Opiate | FITC(3) | BZG   | Propoxy |
| Methaq   | Fent   | Creat   | FITC(4) |       |

The reference molecule, located on the top left corner, was FITC, which is a well-known luminescent substance, diluted to a known concentration so that the light output should lie within a pre-defined range. The camera light output is measured in relative light units (RLUs). If the RLU value of the reference molecule lay outside a specified range, the biochip was rejected, as the processing was deemed to be faulty. Four further spots of FITC (FITC 1 to 4) were also included, to act as further reference molecules (these are referred to below as "correction spots").

The abbreviations used are as follows:

| Barb   | = | Barbiturates |
|--------|---|-------------|
| Benzo  | = | Benzodiazepam |
| Loraz  | = | Lorazepam |
| THC    | = | Tetrahydrocannabinol-9 Carboxylic Acid |
| Amp    | = | Amphetamine |
| Ma     | = | Methamphetamine |
| Meth   | = | Methadone |
| PCP    | = | Phencyclidine |
| BZG    | = | Benzoylegonine |
| Propoxy| = | Propoxyphene |
| Fent   | = | Fentanyl |
| Creat  | = | Creatinine |
| Methaq | = | Methaqualone |

Nine different patient samples were added, one per biochip well, and processed with an image being obtained for analysis. The reference molecule was found on each biochip within pre-defined reference molecule search windows, and screened against pre-defined criteria on RLU value, area (number of pixels), and X/Y aspect ratio. All the reference molecules fell within the predefined RLU limits.

A small degree of image rotation was evident. With the reference molecule on each biochip having been found within the appropriate pre-defined window, the analyte windows were automatically aligned with the DTRs and imaging carried out.

The image was processed automatically, by first carrying out morphological processing, via a series of image opening and closing operations, to calculate the background image from the raw image. The calculated background image was then subtracted from the raw image, to give the background-subtracted image; this removes any fluctuations in signal level due to background variations. Finally, a series of threshold values were used on the background-subtracted image, to define what pixels were above each threshold, so allowing entities of interest to be located. The highest threshold was examined first, and contiguous (discrete) objects found by various blob analysis techniques. The thresholds were lowered progressively, until all the DTRs measurable (i.e. above the lowest threshold, which was set according to the noise level variation of the CCD camera) had been identified. The centroid of each entity was calculated to serve as a location marker for the entity.

Figure 8:
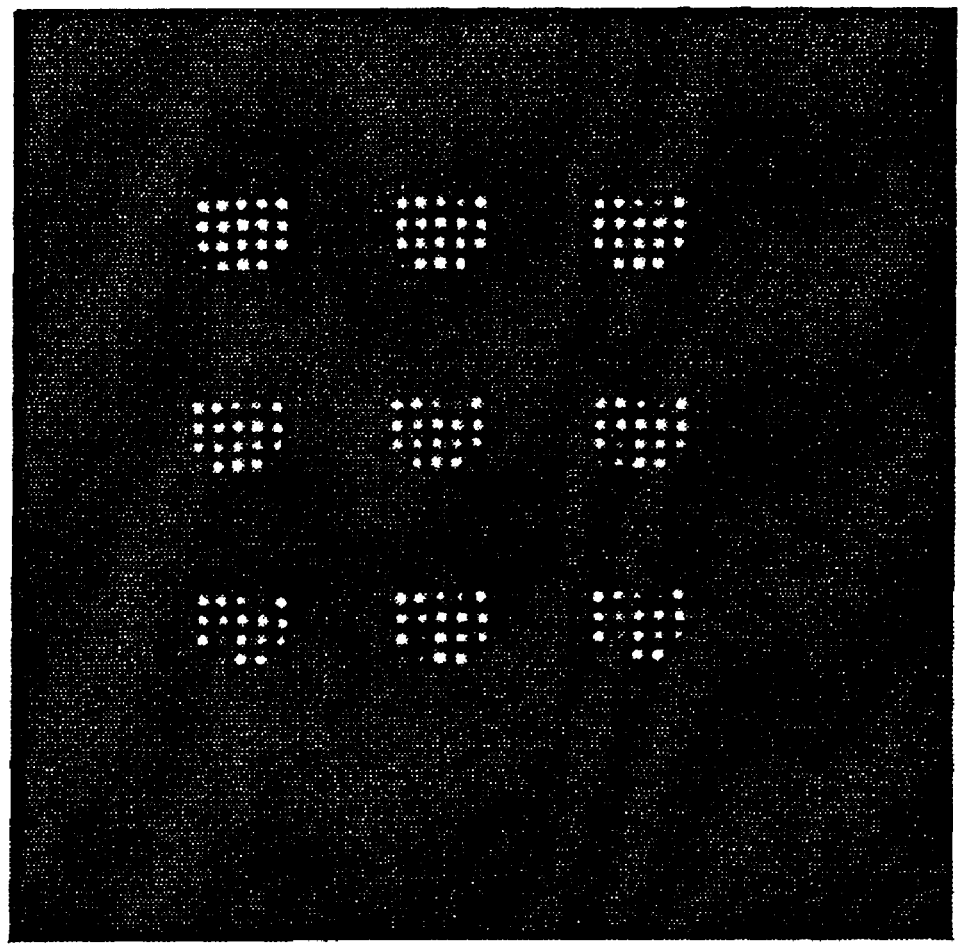
FIG. 8 shows an image obtained in an assay of various analytes, after alignment of inspection windows using a reference molecule.

The RLU values of all detected entities were calculated according to standard methods. The peak light level within the boundary of each entity was found and then a threshold set for each entity at 20% below the peak pixel RLU value. Only those pixels of an entity above the threshold of 20% below the entity peak RLU were used in the subsequent calculation of the average RLU value for that entity. An image of the biochips is shown in FIG. 8.

Each aligned analyte window was checked to ensure that the centroid of an entity lay within its boundaries. If so, that entity was designated to be for the analyte-type assigned to that window. Hence, each entity was identified as being one analyte-type. The correction spots on the nine biochips were then screened against the same criteria as the reference spots, and all correction spots were found to have RLU values within the prescribed limits, so allowing each chip to be designated as of acceptable quality for processing. The average RLU values of the identified entities within each aligned analyte window were then displayed for each processed biochip.

The results for the first biochip, in the top left of the rack, are shown in Table 1.

TABLE 1

| Entity | Area | Centroid X | Centroid Y | RLU | Chip | Type |
|--------|------|------------|------------|-----|------|------|
| 1  | 12 | 102 | 109 | 892      | Chip 1 | Reference |
| 2  | 14 | 112 | 108 | 1007     |        | Barb |
| 3  | 10 | 123 | 108 | 669      |        | Benzo |
| 4  | 5  | 134 | 108 | 367.5    |        | Loraz |
| 5  | 13 | 145 | 108 | 1012.167 |        | THC |
| 6  | 12 | 102 | 120 | 1164.75  |        | Amp |
| 7  | 13 | 114 | 120 | 1132.25  |        | Ma |
| 8  | 16 | 124 | 118 | 1230.667 |        | Methad |
| 9  | 14 | 135 | 118 | 1036.714 |        | PCP |
| 10 | 9  | 146 | 119 | 530      |        | Correction |
| 11 | 12 | 102 | 130 | 715      |        | Correction |
| 12 | 12 | 113 | 130 | 705      |        | Opiate |
| 13 | 9  | 124 | 130 | 529.6667 |        | Correction |
| 14 | 12 | 134 | 130 | 704.25   |        | BZG |
| 15 | 12 | 146 | 130 | 827      |        | Propoxy |
| 16 | 9  | 113 | 141 | 505.125  |        | Fent |
| 17 | 15 | 124 | 140 | 1357.5   |        | Creat |
| 18 | 12 | 134 | 140 | 762      |        | Correction |
| 19 | 3  | 103 | 141 | 58.33333 |        | Methaq |

These RLU values can be compared against measured light output curves as a function of analyte concentration, to determine the concentration of each analyte. An industry standard on threshold concentration for each analyte can then be applied to the determined concentration, to give a positive or negative result, as appropriate.

What is claimed is:

1. A method for imaging an array of discrete reaction sites on the surface of a solid support to detect the presence of molecules in reaction sites on the array, comprising:
   (i) imaging the array,
   (ii) locating a reference signal, using a reference search window, from a reference molecule in a reference reaction site at a known position in the array,
   (iii) aligning a reference inspection window based on location of the signal,
   (iv) separately aligning individual inspection windows of each of the discrete reaction sites with location of the reference molecule, and
   (v) determining the amount of detectable signal in each of the reference inspection window and the individual inspection windows of the discrete reaction sites, to detect the presence of the molecules,
   wherein said molecules are detectably-labelled, and
   wherein each of the individual inspection windows corresponds to each of the discrete reaction sites.

2. A method according to claim 1, wherein the reference inspection window defines a two-dimensional array of pixels and locating is carried out by scanning diagonally the array of pixels and determining values for the pixels.

3. A method according to claim 1, wherein, after locating the reference signal, the reference inspection window is repositioned or enlarged so that one or more of the discrete reaction sites is also located within the window, locating the one or more sites and, by reference to the reference signal and the one or more sites, aligning a further inspection window in registration with each reaction site of the array.

4. A method according to claim 1, wherein step (i) further comprises locating a second reference molecule in a reference reaction site at a known position in the array, and aligning the individual inspection windows of the discrete reaction sites by reference to both the location of the first reference molecule and the location of the second reference molecules.

5. A method according to claim 1, wherein imaging is carried out by detecting emitted radiation.

6. A method according to claim 5, wherein the radiation is chemiluminescent, bioluminescent or fluorescent.

7. A method according to claim 1, wherein the molecules of the array are capable of reacting with an analyte.

8. A method according to claim 1, wherein the molecules of the array are polynucleotides, antibodies, proteins or organic compounds.

9. A method according to claim 1, wherein the solid support is less than 1 $cm^2$.

10. A method according to claim 1, wherein the solid support is a ceramic, silicon or glass material.

11. A method according to claim 1, wherein the molecules of the array are covalently attached to the surface of the solid support.

12. A method according to claim 1, wherein the signal located in step (ii) must be above a pre-defined value in order to proceed with the remaining steps.

* * * * *